(12) United States Patent
Valdez

(10) Patent No.: US 11,857,416 B2
(45) Date of Patent: Jan. 2, 2024

(54) CATHETER ASSEMBLY

(71) Applicant: Edwards Lifesciences Corporation, Irvine, CA (US)

(72) Inventor: Michael G. Valdez, Riverside, CA (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 891 days.

(21) Appl. No.: 16/839,501

(22) Filed: Apr. 3, 2020

(65) Prior Publication Data

US 2020/0229923 A1    Jul. 23, 2020

Related U.S. Application Data

(63) Continuation of application No. PCT/US2018/053532, filed on Sep. 28, 2018.

(60) Provisional application No. 62/573,883, filed on Oct. 18, 2017.

(51) Int. Cl.
*A61F 2/24* (2006.01)

(52) U.S. Cl.
CPC .......... *A61F 2/2436* (2013.01); *A61F 2/2433* (2013.01); *A61F 2/2439* (2013.01)

(58) Field of Classification Search
CPC ...... A61F 2/2436; A61F 2/243; A61F 2/2466; A61F 2/2433; A61F 2/2439; A61F 2/9522; A61F 2002/9665; A61F 2002/9505; A61F 2/2427; A61F 2250/0006; A61B 2017/00243; A61B 2017/00318; A61M 25/0105; A61M 25/0147

USPC ...................................................... 623/2.11
See application file for complete search history.

(56) References Cited

U.S. PATENT DOCUMENTS

| 519,297 A | 5/1894 | Bauer |
| 4,035,849 A | 7/1977 | Angell et al. |
| 4,592,340 A | 6/1986 | Boyles |
| 4,955,895 A | 9/1990 | Sugiyama et al. |
| 4,994,077 A | 2/1991 | Dobben |
| 5,059,177 A | 10/1991 | Towne et al. |
| 5,176,698 A | 1/1993 | Burns et al. |
| 5,192,297 A | 3/1993 | Hull |
| 5,266,073 A | 11/1993 | Wall |
| 5,325,845 A | 7/1994 | Adair |

(Continued)

FOREIGN PATENT DOCUMENTS

| CN | 104470471 A | 3/2015 |
| DE | 19532846 A1 | 3/1997 |

(Continued)

*Primary Examiner* — Brooke Labranche
*Assistant Examiner* — Lauren Dubose
(74) *Attorney, Agent, or Firm* — Edwards Lifesciences

(57) ABSTRACT

Embodiments of a catheter assembly are disclosed. The catheter assembly comprises a shaft; at least one connector assembly. The connector assembly can comprise a first connector portion and a second connector portion, wherein the first connector portion is fixedly coupled to a distal end of the shaft, and is coupled to the second connector portion with a limited degree of freedom of movement by at least one radially extending pin retained within at least one slot on the second connector portion. The at least one slot can have an oversized circumferential dimension that allows limited rotation of the second connector portion relative to the first connector portion about a longitudinal axis of the shaft.

18 Claims, 6 Drawing Sheets

(56) References Cited

U.S. PATENT DOCUMENTS

| | | | |
|---|---|---|---|
| 5,358,496 A | 10/1994 | Ortiz et al. |
| 5,411,552 A | 5/1995 | Andersen et al. |
| 5,554,185 A | 9/1996 | Block et al. |
| 5,591,195 A | 1/1997 | Taheri et al. |
| 5,599,305 A | 2/1997 | Hermann et al. |
| 5,618,300 A | 4/1997 | Marin et al. |
| 5,632,760 A | 5/1997 | Sheiban et al. |
| 5,639,274 A | 6/1997 | Fischell et al. |
| 5,728,068 A | 3/1998 | Leone et al. |
| 5,749,890 A | 5/1998 | Shaknovich |
| 5,782,809 A | 7/1998 | Umeno et al. |
| 5,824,044 A | 10/1998 | Quiachon et al. |
| 5,840,081 A | 11/1998 | Andersen et al. |
| 5,908,405 A | 6/1999 | Imran et al. |
| 5,916,147 A | 6/1999 | Boury |
| 5,961,536 A | 10/1999 | Mickley et al. |
| 5,968,068 A | 10/1999 | Dehdashtian et al. |
| 6,019,777 A | 2/2000 | Mackenzie |
| 6,027,510 A | 2/2000 | Alt |
| 6,033,381 A | 3/2000 | Kontos |
| 6,143,016 A | 11/2000 | Bleam et al. |
| 6,162,208 A | 12/2000 | Hipps |
| 6,168,614 B1 | 1/2001 | Andersen et al. |
| 6,174,327 B1 | 1/2001 | Mertens et al. |
| 6,217,585 B1 | 4/2001 | Houser et al. |
| 6,235,050 B1 | 5/2001 | Quiachon et al. |
| 6,251,092 B1 | 6/2001 | Qin et al. |
| 6,379,372 B1 | 4/2002 | Dehdashtian et al. |
| 6,383,171 B1 | 5/2002 | Gifford et al. |
| 6,454,799 B1 | 9/2002 | Schreck |
| 6,458,153 B1 | 10/2002 | Bailey et al. |
| 6,461,382 B1 | 10/2002 | Cao |
| 6,471,672 B1 | 10/2002 | Brown et al. |
| 6,500,147 B2 | 12/2002 | Omaleki et al. |
| 6,514,228 B1 | 2/2003 | Hamilton et al. |
| 6,527,979 B2 | 3/2003 | Constantz et al. |
| 6,579,305 B1 | 6/2003 | Ashinski |
| 6,582,462 B1 | 6/2003 | Andersen et al. |
| 6,652,578 B2 | 11/2003 | Bailey et al. |
| 6,730,118 B2 | 5/2004 | Spenser et al. |
| 6,733,525 B2 | 5/2004 | Yang et al. |
| 6,764,504 B2 | 7/2004 | Wang et al. |
| 6,767,362 B2 | 7/2004 | Schreck |
| 6,830,584 B1 | 12/2004 | Seguin |
| 6,893,460 B2 | 5/2005 | Spenser et al. |
| 6,908,481 B2 | 6/2005 | Cribier |
| 7,011,094 B2 | 3/2006 | Rapacki et al. |
| 7,018,406 B2 | 3/2006 | Seguin et al. |
| 7,018,408 B2 | 3/2006 | Bailey et al. |
| 7,137,993 B2 | 11/2006 | Acosta et al. |
| 7,276,084 B2 | 10/2007 | Yang et al. |
| 7,318,278 B2 | 1/2008 | Zhang et al. |
| 7,320,702 B2 | 1/2008 | Hammersmark et al. |
| 7,320,704 B2 | 1/2008 | Lashinski et al. |
| 7,374,571 B2 | 5/2008 | Pease et al. |
| 7,393,360 B2 | 7/2008 | Spenser et al. |
| 7,435,257 B2 | 10/2008 | Lashinski et al. |
| 7,510,575 B2 | 3/2009 | Spenser et al. |
| 7,585,321 B2 | 9/2009 | Cribier |
| 7,594,926 B2 | 9/2009 | Linder et al. |
| 7,597,709 B2 | 10/2009 | Goodin |
| 7,618,446 B2 | 11/2009 | Andersen et al. |
| 7,780,723 B2 | 8/2010 | Taylor |
| 7,785,366 B2 | 8/2010 | Maurer et al. |
| 7,959,661 B2 | 6/2011 | Hijlkema et al. |
| 8,029,556 B2 | 10/2011 | Rowe |
| 8,167,932 B2 | 5/2012 | Bourang et al. |
| RE43,882 E | 12/2012 | Hopkins et al. |
| 8,449,606 B2 | 5/2013 | Eliasen et al. |
| 8,475,523 B2 | 7/2013 | Duffy |
| 8,568,472 B2 | 10/2013 | Marchand et al. |
| 9,061,119 B2 | 6/2015 | Le et al. |
| 9,119,716 B2 | 9/2015 | Lee et al. |
| 9,795,477 B2 | 10/2017 | Tran et al. |
| 2001/0002445 A1 | 5/2001 | Vesely |
| 2001/0007082 A1 | 7/2001 | Dusbabek et al. |
| 2002/0032481 A1 | 3/2002 | Gabbay |
| 2002/0058995 A1 | 5/2002 | Stevens |
| 2002/0165461 A1 | 11/2002 | Hayzelden et al. |
| 2003/0040792 A1 | 2/2003 | Gabbay |
| 2003/0050694 A1 | 3/2003 | Yang et al. |
| 2003/0120341 A1 | 6/2003 | Shennib et al. |
| 2004/0093061 A1 | 5/2004 | Acosta et al. |
| 2004/0133263 A1 | 7/2004 | Dusbabek et al. |
| 2004/0143197 A1 | 7/2004 | Soukup et al. |
| 2004/0186563 A1 | 9/2004 | Lobbi |
| 2004/0186565 A1 | 9/2004 | Schreck |
| 2004/0260389 A1 | 12/2004 | Case et al. |
| 2005/0080474 A1 | 4/2005 | Andreas et al. |
| 2005/0096736 A1 | 5/2005 | Osse et al. |
| 2005/0137689 A1 | 6/2005 | Salahieh et al. |
| 2005/0149160 A1 | 7/2005 | McFerran |
| 2005/0203614 A1 | 9/2005 | Forster et al. |
| 2005/0203617 A1 | 9/2005 | Forster et al. |
| 2005/0245894 A1 | 11/2005 | Zadno-Azizi |
| 2006/0025857 A1 | 2/2006 | Bergheim et al. |
| 2006/0100687 A1* | 5/2006 | Fahey ............... A61M 25/0051 606/191 |
| 2006/0282150 A1 | 12/2006 | Olson et al. |
| 2007/0005131 A1 | 1/2007 | Taylor |
| 2007/0073389 A1 | 3/2007 | Bolduc et al. |
| 2007/0088431 A1 | 4/2007 | Bourang et al. |
| 2007/0112422 A1 | 5/2007 | Dehdashtian |
| 2007/0203575 A1 | 8/2007 | Forster et al. |
| 2007/0219612 A1 | 9/2007 | Andreas et al. |
| 2007/0239254 A1 | 10/2007 | Chia et al. |
| 2007/0244546 A1 | 10/2007 | Francis |
| 2007/0265700 A1 | 11/2007 | Eliasen et al. |
| 2008/0065011 A1 | 3/2008 | Marchand et al. |
| 2008/0125853 A1 | 5/2008 | Bailey et al. |
| 2008/0294230 A1 | 11/2008 | Parker |
| 2009/0024428 A1 | 1/2009 | Hudock, Jr. |
| 2009/0069889 A1 | 3/2009 | Suri et al. |
| 2009/0138079 A1 | 5/2009 | Tuval et al. |
| 2009/0157175 A1 | 6/2009 | Benichou |
| 2009/0192585 A1 | 7/2009 | Bloom et al. |
| 2009/0228093 A1 | 9/2009 | Taylor et al. |
| 2009/0276040 A1 | 11/2009 | Rowe et al. |
| 2009/0281619 A1 | 11/2009 | Le et al. |
| 2009/0299456 A1 | 12/2009 | Melsheimer |
| 2009/0319037 A1 | 12/2009 | Rowe et al. |
| 2010/0030318 A1 | 2/2010 | Berra |
| 2010/0036472 A1 | 2/2010 | Papp |
| 2010/0036473 A1 | 2/2010 | Roth |
| 2010/0049313 A1 | 2/2010 | Alon et al. |
| 2010/0076402 A1 | 3/2010 | Mazzone et al. |
| 2010/0076541 A1 | 3/2010 | Kumoyama |
| 2010/0082089 A1 | 4/2010 | Quadri et al. |
| 2010/0094394 A1 | 4/2010 | Beach et al. |
| 2010/0121425 A1 | 5/2010 | Shimada |
| 2010/0145431 A1 | 6/2010 | Wu et al. |
| 2010/0161036 A1 | 6/2010 | Pintor et al. |
| 2010/0174363 A1 | 7/2010 | Castro |
| 2010/0198347 A1 | 8/2010 | Zakay et al. |
| 2010/0274344 A1 | 10/2010 | Dusbabek et al. |
| 2010/0318067 A1* | 12/2010 | Klima ............... A61M 25/0138 604/528 |
| 2011/0015729 A1 | 1/2011 | Jimenez et al. |
| 2011/0054596 A1 | 3/2011 | Taylor |
| 2011/0112632 A1* | 5/2011 | Chau .................... A61F 2/2436 623/2.11 |
| 2011/0137331 A1 | 6/2011 | Walsh et al. |
| 2011/0160846 A1 | 6/2011 | Bishop et al. |
| 2011/0307049 A1 | 12/2011 | Kao |
| 2012/0123529 A1 | 5/2012 | Levi et al. |
| 2012/0239142 A1 | 9/2012 | Liu et al. |
| 2013/0030519 A1 | 1/2013 | Tran et al. |
| 2013/0297012 A1* | 11/2013 | Willard ................ A61F 2/2427 623/2.11 |
| 2013/0317598 A1 | 11/2013 | Rowe et al. |
| 2014/0296962 A1 | 10/2014 | Cartledge et al. |
| 2015/0245934 A1 | 9/2015 | Lombardi et al. |
| 2015/0297346 A1 | 10/2015 | Duffy et al. |

(56) References Cited

U.S. PATENT DOCUMENTS

| | | |
|---|---|---|
| 2017/0065415 A1 | 3/2017 | Rupp et al. |
| 2018/0153689 A1 | 6/2018 | Maimon et al. |
| 2018/0344456 A1 | 12/2018 | Barash et al. |

FOREIGN PATENT DOCUMENTS

| | | |
|---|---|---|
| DE | 19907646 A1 | 8/2000 |
| EP | 0592410 B1 | 10/1995 |
| EP | 0850607 A1 | 7/1998 |
| FR | 2815844 A1 | 5/2002 |
| JP | 2005193032 A | 7/2005 |
| JP | 2012500665 A | 1/2012 |
| JP | 2013528112 A | 7/2013 |
| WO | 9117720 A1 | 11/1991 |
| WO | 9829057 A1 | 7/1998 |
| WO | 9912483 A1 | 3/1999 |
| WO | 0149213 A2 | 7/2001 |
| WO | 0154625 A1 | 8/2001 |
| WO | 0176510 A2 | 10/2001 |
| WO | 0222054 A1 | 3/2002 |
| WO | 0236048 A1 | 5/2002 |
| WO | 0247575 A2 | 6/2002 |
| WO | 02060352 | 8/2002 |
| WO | 03030776 A2 | 4/2003 |
| WO | 03047468 A1 | 6/2003 |
| WO | 2004019825 A1 | 3/2004 |
| WO | 2005037140 A1 | 4/2005 |
| WO | 2005084595 A1 | 9/2005 |
| WO | 2006032051 A2 | 3/2006 |
| WO | 2006111391 A1 | 10/2006 |
| WO | 2006138173 A2 | 12/2006 |
| WO | 2005102015 A3 | 4/2007 |
| WO | 2007047488 A2 | 4/2007 |
| WO | 2007067942 A1 | 6/2007 |
| WO | 2010022138 A2 | 2/2010 |
| WO | 2010121076 A2 | 10/2010 |
| WO | 2011150399 A1 | 12/2011 |
| WO | 2011156533 A2 | 12/2011 |

\* cited by examiner

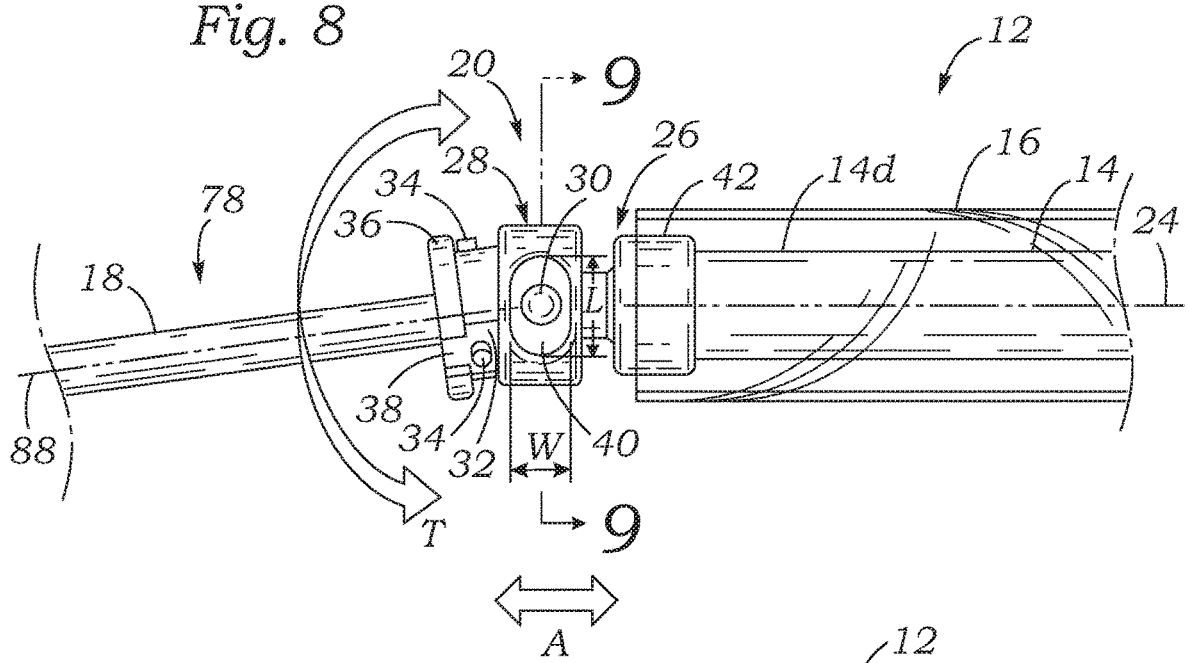
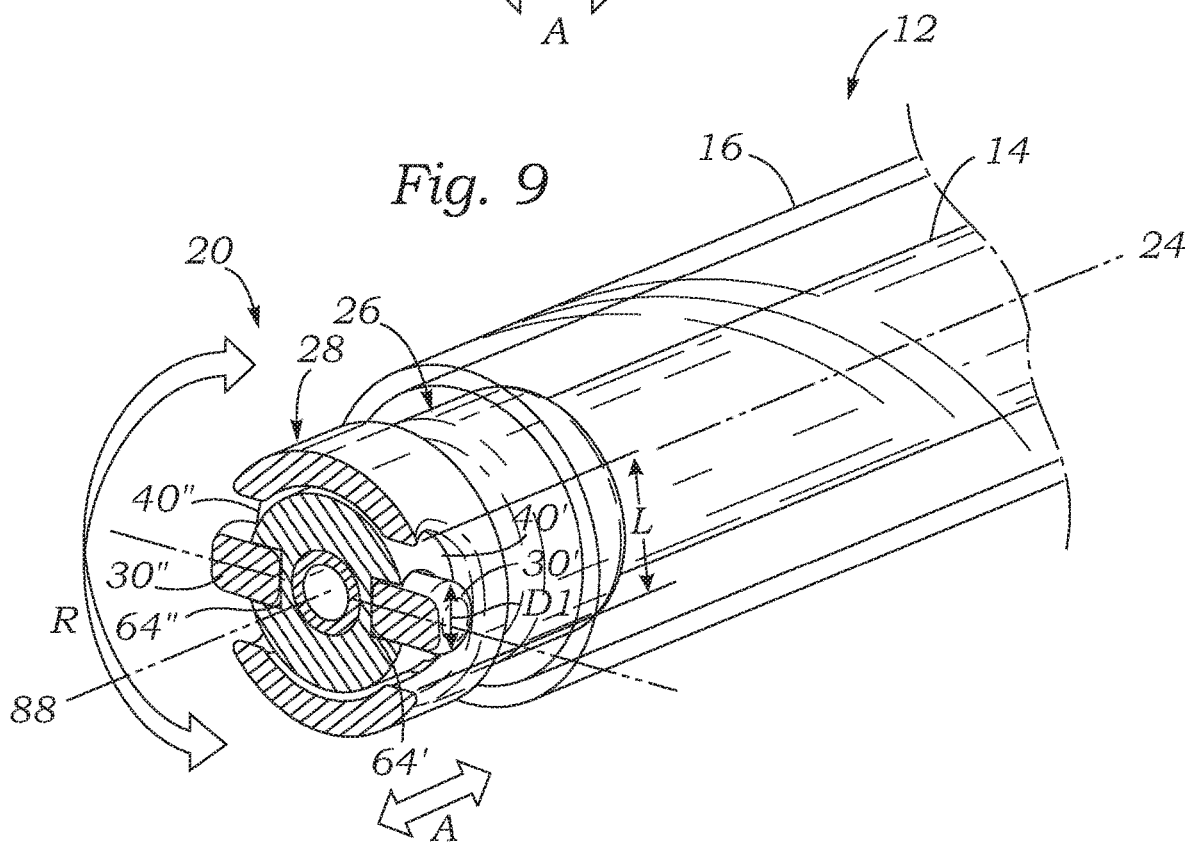

CATHETER ASSEMBLY

RELATED APPLICATIONS

This application is a continuation of International Application No. PCT/US2018/053532, filed Sep. 28, 2018, which claims the benefit of U.S. Provisional Patent Application No. 62/573,883, filed on Oct. 18, 2017. The foregoing applications are incorporated by reference in their entirety herein for all purposes.

FIELD

The present disclosure concerns embodiments of a catheter assembly, such as a delivery apparatus for implanting a prosthetic heart valve.

BACKGROUND

Endovascular delivery devices, such as catheters, can be used in various procedures to deliver prosthetic medical devices or instruments to locations inside the body that are not readily accessible by surgery or where access without surgery is desirable. Access to a target location inside the body can be achieved by inserting and guiding the delivery device through a pathway or lumen in the body, including, but not limited to, a blood vessel, an esophagus, a trachea, any portion of the gastrointestinal tract, a lymphatic vessel, to name a few. For example, a prosthetic heart valve can be mounted in a crimped state on the distal end of a delivery device and advanced through the patient's vasculature (e.g., through a femoral artery and the aorta) until the prosthetic valve reaches the implantation site in the heart. The prosthetic valve can then be expanded to its functional size such as by inflating a balloon on which the prosthetic valve is mounted, or by deploying the prosthetic valve from a sheath of the delivery device so that the prosthetic valve can self-expand to its functional size.

The usefulness of delivery devices is largely limited by the ability of the device to successfully navigate through small vessels and around bends in the vasculature, such as around the aortic arch. Since the path through the patient's vasculature to the intended site is often long and tortuous, steering forces must be transmitted over great distances. It is preferably for a delivery catheter to have sufficient axial strength so that the physician can push through the patient's vasculature via a force applied at the proximal end of the catheter. In addition, the distal part of the delivery catheter preferably includes a steerable section having sufficient flexibility so that it can pass through tortuous anatomy without sacrificing rigidness of the catheter shaft. However, delivery catheters can be too stiff and be difficult to push through the vasculature. Hence, there is a need for delivery catheters with enhanced flexibility.

SUMMARY

This summary is meant to provide some examples and is not intended to be limiting of the scope of the invention in any way. For example, any feature included in an example of this summary is not required by the claims, unless the claims explicitly recite the features. Also, the features, components, steps, concepts, etc. described in examples in this summary and elsewhere in this disclosure can be combined in a variety of ways. Various features and steps as described elsewhere in this disclosure may be included in the examples summarized here.

Disclosed herein are steerable catheter devices and related methods, which can be used to deliver a medical device, tools, agents, or other therapy to a location within a body of a subject. In some implementations, the steerable catheter devices can be used to deliver a medical device through the vasculature, such as to a heart of the subject.

Certain embodiments of the disclosure concern a catheter assembly that includes a shaft and a connector assembly. The connector assembly can include a first connector portion and a second connector portion. The first connector portion can be fixedly coupled to a distal end of the shaft, and is rotatably coupled to the second connector portion by at least one radially extending pin retained within at least one slot on the second connector portion. The at least one slot can have an oversized circumferential dimension that allows limited rotation of the second connector portion relative to the first connector portion about a longitudinal axis of the shaft.

In some embodiments, the at least one slot can be sized to allow limited tilting of the second connector portion with respect to the longitudinal axis of the shaft.

In some embodiments, the at least one slot can have an oversized width in a direction along the longitudinal axis that allows limited axial movement of the first connector portion relative to the second connector portion.

In some embodiments, the at least one slot can include first and second slots and the at least one pin comprises first and second pins disposed in the first and second slots, respectively.

In some embodiments, each slot can have an arc length around the longitudinal axis of less than 180 degrees.

In the foregoing embodiments, the first connector portion can include a distal end portion that extends into an axial bore of the second connector portion, and the at least one pin can extend radially outwardly from the distal end portion into the at least one slot in the second connector portion.

In the foregoing embodiments, the second connector portion can include one or more attachment features configured to form a releasable attachment with corresponding retaining arms of an implantable medical device.

In certain embodiments, the one or more attachment features can include one or more recesses configured to receive the one or more retaining arms of the implantable medical device.

In certain embodiments, the catheter assembly can further include an outer sheath configured to extend over the connector assembly and the implantable medical device so as to retain the implantable medical device in a radially compressed state within the sheath when the retaining arms are in engagement with the attachment features of the second connector portion.

In the foregoing embodiments, the catheter assembly can further include another shaft having a proximal end connected to the second connector portion.

Certain embodiments of the disclosure also concern a delivery apparatus for delivering an implantable device via a patient's vasculature. The delivery apparatus includes an outer sheath, a shaft extending through the outer sheath; and a connector assembly. The connector assembly can include a first connector portion and a second connector portion. The first connector portion can be fixedly coupled to a distal end of the shaft. The second connector portion can be coupled to the first connector portion such that the second connector portion can rotate relative to the first connector portion about a longitudinal axis of the shaft and can tilt with respect to the longitudinal axis of the shaft. The second connector portion can include one or more attachment features configured to form a releasable attachment with corresponding retaining arms of a radially expandable implantable medical device. The outer sheath can be configured to extend over the connector assembly and the implantable medical device so as to retain the implantable medical device in a radially compressed state within the sheath when the retaining arms of the implantable medical device are placed in engagement with the attachment features of the second connector portion.

In some embodiments, the second connector portion can be coupled to the first connector portion such that the second connector portion can move axially relative to the first connector portion a limited amount in a direction parallel to the longitudinal axis.

In some embodiments, the second connector portion can be coupled to the first connector portion by at least one radially extending pin retained within at least one slot on the second connector portion.

In some embodiments, the second connector portion can be coupled to the first connector portion by at least one radially extending pin retained within at least one slot on the first connector portion.

In some embodiments, the at least one slot can have an oversized circumferential dimension that allows limited rotation of the second connector portion relative to the first connector portion about the longitudinal axis of the shaft.

In some embodiments, the at least one slot can be sized to allow limited tilting of the second connector portion with respect to the longitudinal axis of the shaft.

In some embodiments, the at least one slot can have an oversized width in a direction along the longitudinal axis that allows limited axial movement of the first connector portion relative to the second connector portion.

In some embodiments, the at least one slot can include first and second slots and the at least one pin can include first and second pins disposed in the first and second slots, respectively, and the first slot being opposite the second slot with respect to the longitudinal axis.

In some embodiments, the attachment features of the second connector portion can include one or more recesses configured for receiving one or more retaining arms of the implantable device.

Further, certain embodiments of the disclosure also concern an assembly including an outer sheath, a first shaft extending through the outer sheath, a second shaft extending through the first shaft, a nose cone mounted on a distal end portion of the second shaft, a connector assembly, and a radially expandable and compressible prosthetic heart valve. The connector assembly can include a proximal connector portion and a distal connector portion. The proximal connector portion can be fixedly coupled to a distal end of first shaft. The distal connector portion can be rotatably coupled to the proximal connector portion by at least a pin retained within a slot in the distal connector portion. The slot can have an oversized circumferential dimension that allows limited rotation of the distal connector portion relative to the proximal connector portion about a longitudinal axis of the first shaft, limited tilting of the distal connector portion with respect to the longitudinal axis, and limited axial movement of the distal connector portion relative to the proximal connector portion in a direction parallel to the longitudinal axis. The distal connector portion can include one or more attachment features. The prosthetic heart valve can be retained in a radially compressed state within the sheath and having one or more retaining arms that engage respective attachment features of the distal connector portion.

The foregoing and other objects, features, and advantages of the invention will become more apparent from the following detailed description, which proceeds with reference to the accompanying figures.

BRIEF DESCRIPTION OF THE DRAWINGS

The disclosed devices/apparatuses, systems, methods, etc. may be better understood with reference to the following drawings.

FIG. 8 shows a side elevation view of the exemplary connector assembly depicted in FIG. 4 and illustrates its tilting movement.

FIG. 9 shows a cross-sectional view of the exemplary connector assembly depicted in FIG. 4 and illustrates its rotational movement.

Figure 1:
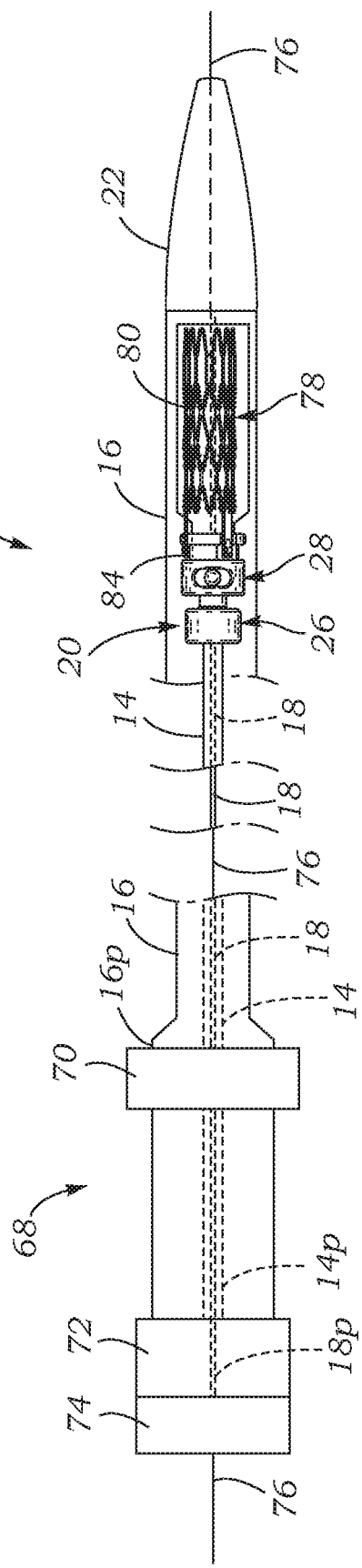
FIG. 1 shows a side elevation view of an exemplary catheter assembly including a delivery apparatus and a prosthetic heart valve that is in a radially compressed state.

While the present disclosure is subject to various modifications and alternative forms, specific embodiments thereof have been shown by way of example in the drawings and will herein be described in detail. The invention should be understood to not be limited to the particular forms disclosed, but to cover all modifications, equivalents, and alternatives falling within the spirit and scope of the present disclosure.

DETAILED DESCRIPTION

The following description and accompanying figures, which describe and show certain embodiments, are made to demonstrate, in a non-limiting manner, several possible configurations of systems, platforms, devices, methods, etc. that may be used for various aspects and features of the present disclosure.

In some embodiments, a delivery apparatus that can be used to deliver a medical device, tools, agents, or other therapy to a location within the body of a subject can include one or more steerable catheters and/or sheaths. Examples of procedures in which steerable catheters and sheaths are useful include cardiovascular, neurological, urological, gynecological, fertility (e.g., in vitro fertilization, artificial insemination), laparoscopic, arthroscopic, transesophageal, transvaginal, transvesical, transrectal, and procedures including access in any body duct or cavity. Particular examples include placing implants, including stents, grafts, embolic coils, and the like; positioning imaging devices and/or components thereof, including ultrasound transducers; and positioning energy sources, for example, for performing lithotripsy, RF sources, ultrasound emitters, electromagnetic sources, laser sources, thermal sources, and the like.

In some embodiments, the delivery apparatus can include a steerable shaft such as a guide sheath having one or more delivery catheters coaxially disposed within the guide sheath. The delivery apparatus can comprise one or more eccentrically positioned pull wires configured to cause the steerable shaft to curve in a given direction, or to straighten. In some embodiments, the delivery apparatus can be used to deliver a medical device through the vasculature, such as to a heart of the subject. In certain configurations, a balloon-inflatable or self-expandable prosthetic heart valve can be mounted on a distal portion of the delivery apparatus. Exemplary configurations of the prosthetic heart valve and implant catheter are further disclosed in U.S. Patent Application Publication Nos. 2013/0030519, 2012/0123529, 2010/0036484, 2010/0049313, 2010/0239142, 2009/0281619, 2008/0065011, and 2007/0005131, each of which is incorporated by reference herein. In addition, it should be understood that the delivery apparatus can be used to deliver any of various other implantable devices, such as docking devices, leaflet clips, annuloplasty devices, etc.

Figure 2:
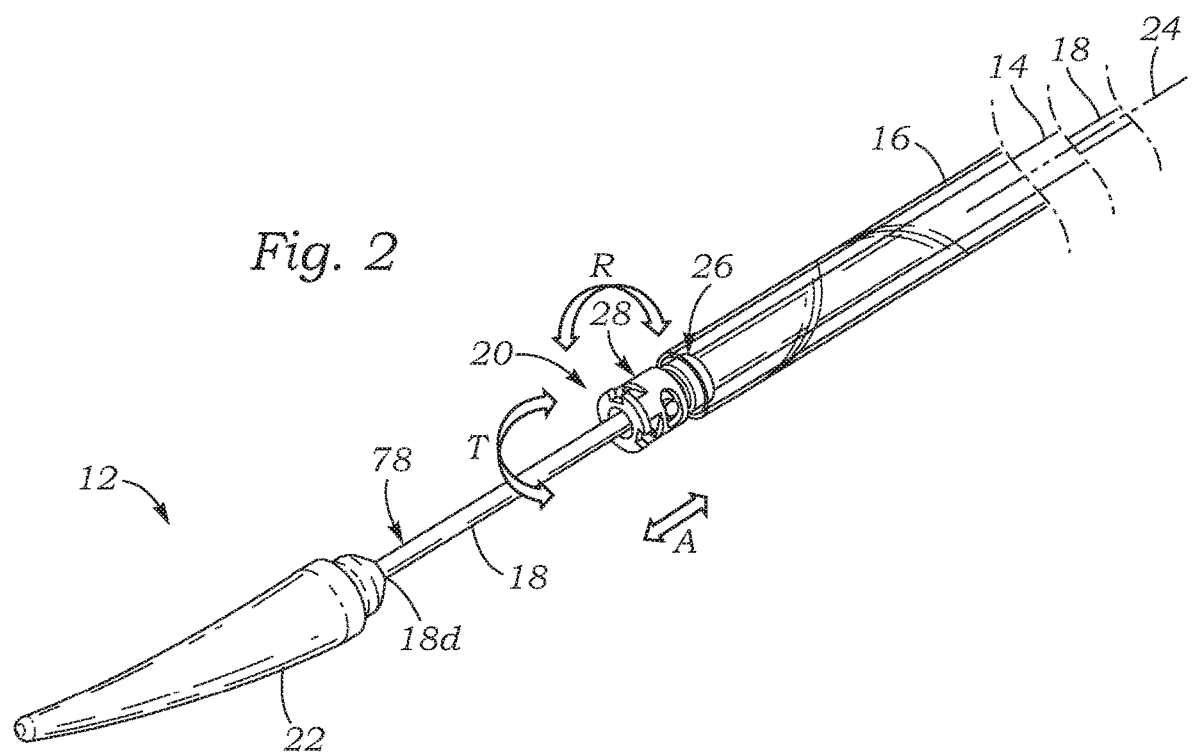
FIG. 2 shows a top perspective view of a distal portion of the exemplary delivery apparatus depicted in FIG. 1.

As an exemplary embodiment, FIG. 1 shows a catheter assembly 10 that includes a prosthetic heart valve 80 mounted on a delivery apparatus 12. FIG. 2 shows a distal portion of the delivery apparatus 12, according to one exemplary embodiment.

As shown, the delivery apparatus 12 can include a first shaft 14, a connector assembly 20 that is coupled to a distal end portion of the first shaft 14, an outer sheath 16 sized to extend over the first shaft 14 and the connector assembly 20, a second shaft 18 (which can also be referred to as an "inner shaft" in the illustrated embodiment) extending through the first shaft 14 and the connector assembly 20, and a nose cone 22 connected to a distal end 18d of the inner shaft 18. A guide wire 76 can extend through the central lumen of the inner shaft 18 and the inner lumen of the nose cone 22, so that the delivery apparatus 12 can be advanced over the guide wire 76 inside the patient's vasculature.

The connector assembly 20 in the illustrated embodiment includes a first connector portion 26 and a second connector portion 28, wherein the first connector portion 26 is positioned proximally relative to the second connector portion 28. The first connector portion 26 (which can be referred to as a "proximal connector portion" in the illustrated embodiment) can be fixedly coupled to the distal end 14d of the first shaft 14, and the first connector portion 26 can be generally coaxial with the first shaft 14. The second connector portion 28 (which can be referred to as a "distal connector portion" in the illustrated embodiment) can be coupled to the first connector portion 26 so as to permit limited movement of the second connector portion relative to the first connector portion.

As indicated in FIG. 2 and described more fully below, the second connector portion 28 can be configured to have one or multiple degrees of freedom to move relative to the first connector portion 26. For example, with respect to the first connector portion 26, the second connector portion 28 can translate axially (in the directions indicated by double-headed arrow A) along the longitudinal axis 24 of the first shaft 14, rotate in a plane that is transverse to the longitudinal axis 24 (in the directions indicated by double-headed arrow R), and/or axially tilt with respect to the longitudinal axis 24 (in the directions indicated by arrow T). Various combinations of degrees of these and/or other freedom of movement are possible.

The delivery apparatus 12 can have a device retaining portion 78 located between the connector assembly 20 and the nose cone 22. The device retaining portion 78 can be configured to accommodate an implantable medical device, such as a prosthetic heart valve 80 (see e.g., FIG. 1), in a radially compressed state within the outer sheath 16. As described herein, the prosthetic heart valve 80 can be balloon inflatable, self-expandable, mechanically-expandable, and/or one or more combinations of these.

As described more fully below, the outer sheath 16 can be configured to move axially (or longitudinally) relative to the first shaft 14 and the second shaft 18 between a first, distal position extending over the device retaining portion 78 and the implantable medical device for delivery through the vasculature of a patient (as shown in FIG. 1) and a second, proximal position in which the distal end of the outer sheath 16 is proximal to the device retaining portion 78 (as shown in FIG. 2) to allow the implantable medical device to be expanded at the desired implantation site, as further described below.

Figure 3:
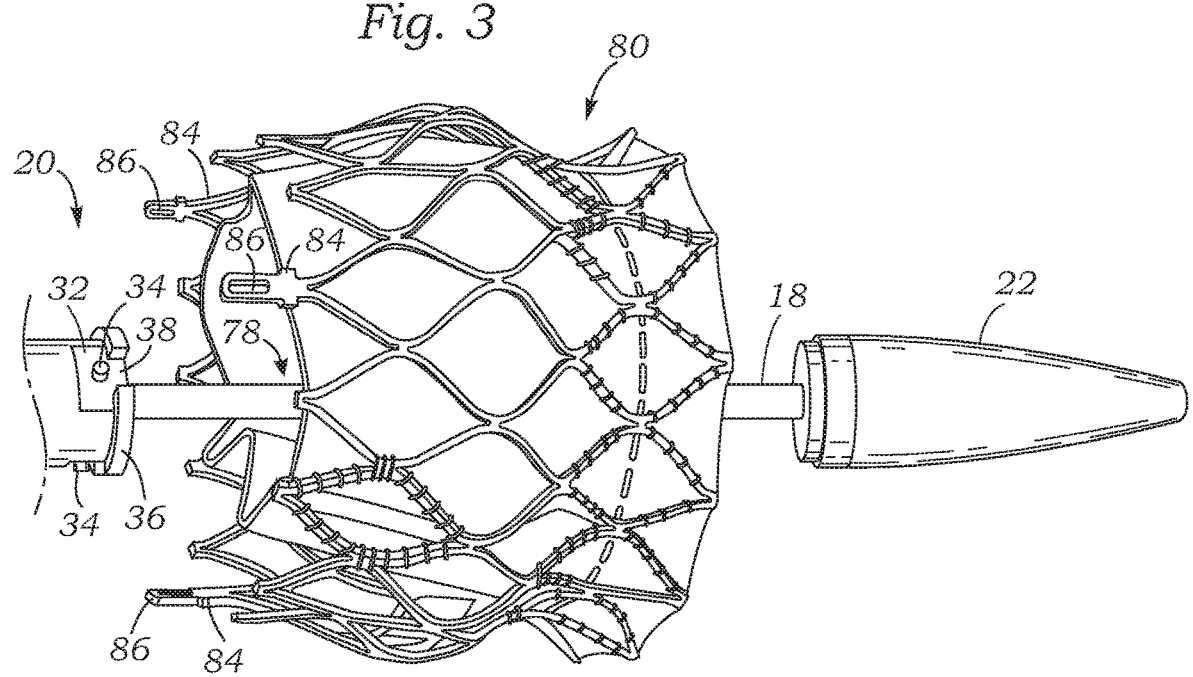
FIG. 3 shows an expanded prosthetic heart valve along a distal portion of the exemplary catheter assembly of FIG. 1.

For example, as shown in FIGS. 1 and 3 and described more fully below, the prosthetic heart valve 80 can have one or more retaining arms 84 that engage respective attachment features of the connector assembly 20. When the prosthetic heart valve 80 is deployed from the sheath (e.g., by sliding the outer sheath 16 proximally or sliding the inner shaft 18 distally), the retaining arms 84 can disengage from respective attachment features. Accordingly, the prosthetic heart valve 80 can be released from the device retaining portion 78, and expanded to its functional size (see e.g., FIG. 3) for deployment at the target site.

In some embodiments, the prosthetic heart valve 80 can be self-expandable such that the prosthetic heart valve 80 automatically expands from the radially compressed state to a radially expanded state once it is deployed from the outer sheath 16. In other embodiments, the prosthetic heart valve 80 can be configured to be expanded by an expansion device (e.g., an inflatable balloon) or combination of expansion devices.

As shown in FIG. 1, the delivery apparatus 12 can include a handle 68 at a proximal end thereof. During delivery of the implantable medical device (e.g., the prosthetic heart valve 80), the handle 68 can be maneuvered by a surgeon to advance and retract the delivery apparatus 12 through the patient's vasculature.

In one exemplary, non-limiting embodiment illustrated in FIG. 1, the handle 68 can include a knob or a plurality of knobs (e.g., 1, 2, 3, 4, or more knobs) for controlling different components or aspects of the delivery apparatus 12. For example, in one embodiment, the proximal end 16p of the outer sheath 16 can be operatively coupled to a first knob 70, the proximal end 14p of the first shaft 14 can be operatively coupled to a second knob 72, and the proximal end 18p of the inner shaft 18 can be operatively coupled to a knob 74. The handle 68 can additionally or alternatively include a button or a plurality of buttons (e.g., 1, 2, 3, 4, or more buttons) for controlling different components or aspects of the delivery apparatus 12.

In some embodiments, operation (e.g., rotational or axial movement) of a knob or button (e.g., the first knob 70) can cause the outer sheath 16 to slide over and retain the implantable medical device (e.g., the prosthetic heart valve 80) or withdraw proximally so as to expose and release the implantable medical device. In some embodiments, operation of the first knob 70 can cause rotational twisting of the outer sheath 16 relative to the first shaft 14 and the inner shaft 18.

In some embodiments, operation (e.g., rotational or axial movement) of a knob or button (e.g., the second knob 72) can cause the first shaft 14 to rotate about and/or slide along its longitudinal axis 24. Because the distal end 14d of the first shaft 14 is fixedly coupled to the first connector portion 26, operation of the second knob 72 can produce limited movement (e.g., rotational and/or axial movement) of the first connector portion 26 relative to the second connector portion 28.

In some embodiments, operation (e.g., rotational or axial movement) of a knob or button (e.g., the third knob 74) can cause the inner shaft 18 (and the nose cone) to slide longitudinally relative to the first shaft 14 and the outer sheath 16. For example, in certain embodiments, the inner shaft 18 can be moved distally to move the nose cone 22 distally relative to the sheath 16 so that the implantable medical device can then be deployed from the sheath.

Further details of the construction of the handle with knobs and the means for operating the handle and knobs are described in U.S. Patent Application Publication Nos. 2013/0030519, 2009/0281619, 2008/0065011, and 2007/0005131, each of which is incorporated by reference herein. Optionally, different components of the delivery apparatus 12 can be controlled by other actuation mechanisms (e.g., other knobs, buttons, joysticks, voice-controlled actuators, touch pads, touch screens, etc.)

Figure 4:
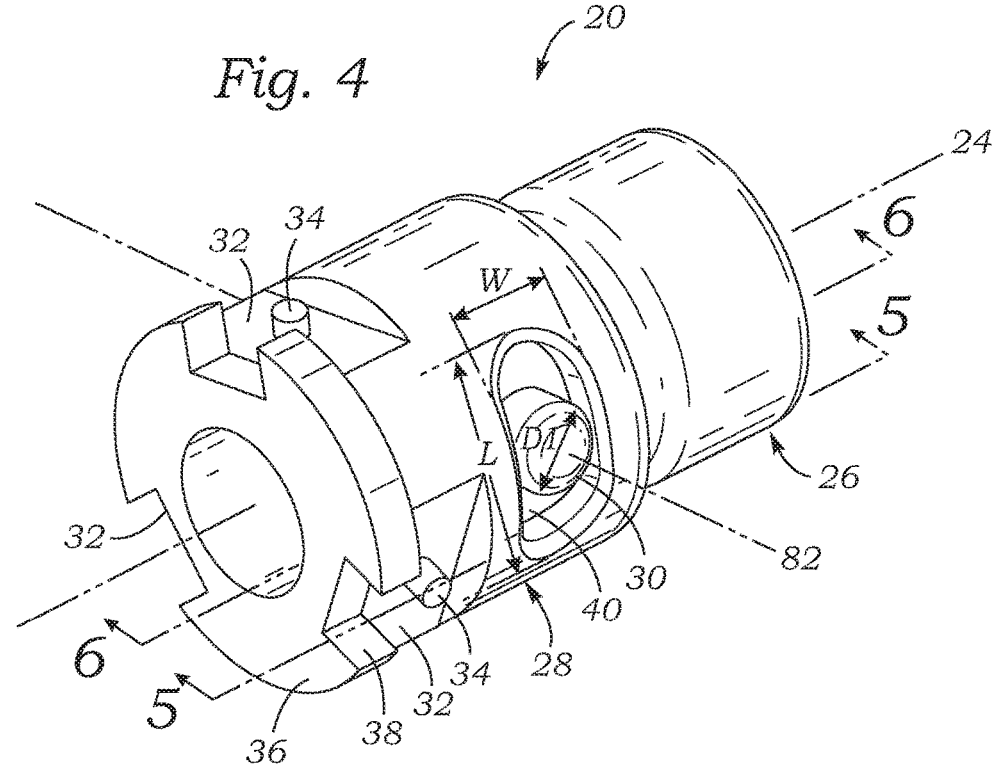
FIG. 4 shows a top perspective view of an exemplary connector assembly included in the exemplary delivery apparatus depicted in FIG. 2.

FIG. 4 shows an exemplary connector assembly 20 in isolation without displaying other parts of the delivery apparatus 12. As shown, the connector assembly 20 can include the first connector portion 26 and the second connector portion 28 that is distal to the first connector portion 26. The first and second connector portions 26, 28 can be generally cylindrical in shape, or can be one or more other shapes. The first and second connector portions 26, 28 can be rotatably coupled to each other by at least one radially extending pin 30 retained within at least one slot 40 formed in the second connector portion 28.

Figure 5:
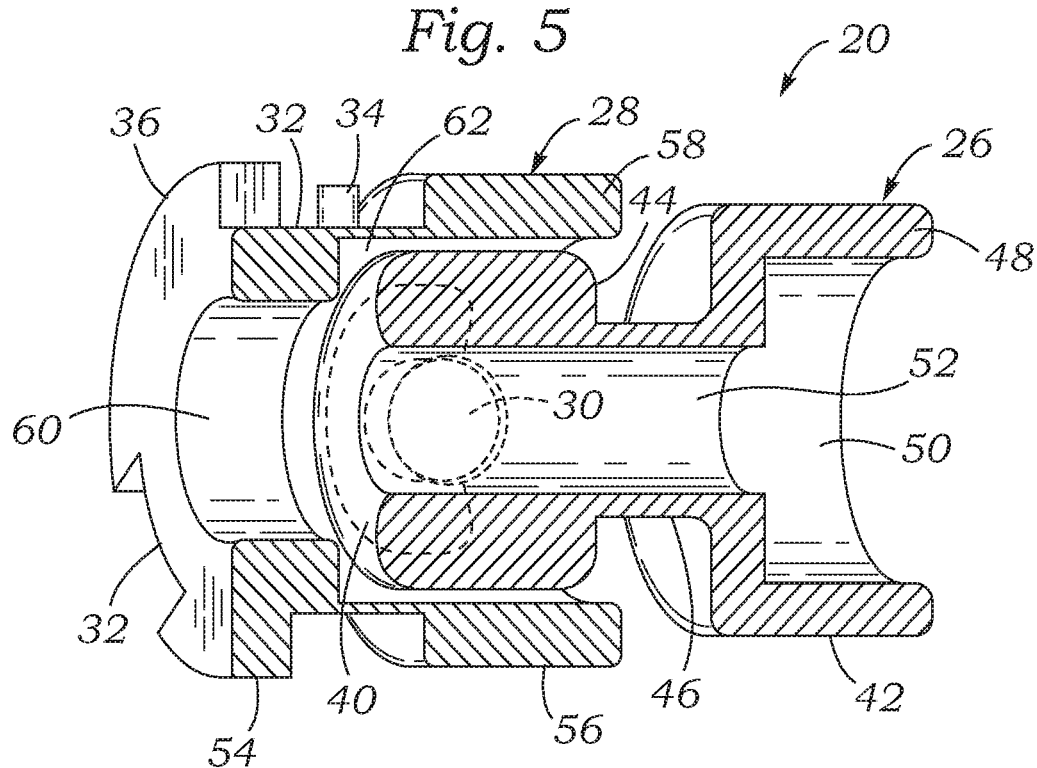
FIG. 5 shows a cross-sectional view of the connector assembly of FIG. 4 taken along line 5-5 of FIG. 4.
Figure 6:
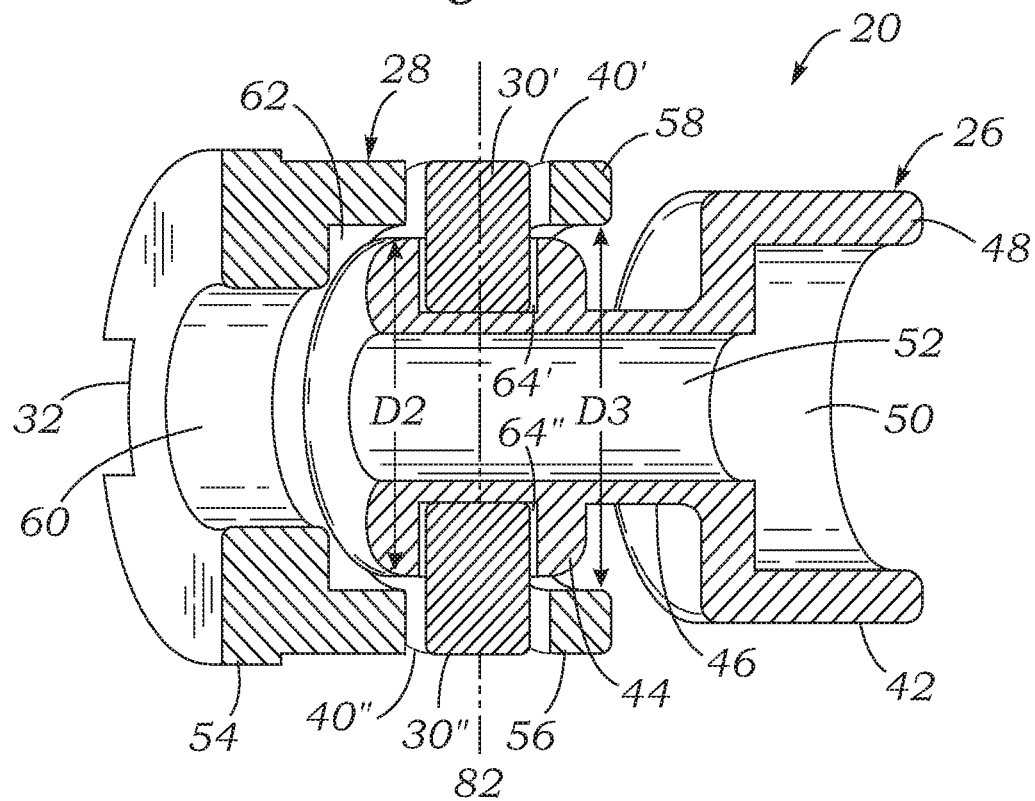
FIG. 6 shows another cross-sectional view of the connector assembly of FIG. 4 taken along line 6-6 of FIG. 4.

FIGS. 5-6 show one exemplary, non-limiting embodiment of the detailed structure of the connector assembly 20. As shown, the first connector portion 26 can include a proximal end portion 42 and a distal end portion 44 connected by an intermediate portion 46. The proximal end portion 42 can be fixedly coupled to the distal end portion 14d of the shaft 14. While various shapes are possible, in one embodiment, each portion 42, 44, 46 has a cylindrical or generally cylindrical shape but can vary in cross-sectional area (e.g., the cross-section of the intermediate portion can have a smaller area, diameter, and/or thickness than the proximal and distal end portions). In some embodiments, each portion 42, 44, 46 can have a non-cylindrical shape (e.g., the cross-sectional shape of the portion can be square, oval, hexagonal, etc.). The first connector portion 26 can comprise a sidewall 48 defining a proximal lumen 50 along the proximal end portion 42 and a distal lumen 52 extending through the intermediate and distal end portions 44, 46. The proximal lumen 50 can have a larger interior dimension (e.g., diameter) than the distal lumen 52. To affix the shaft 14 to the first connector portion 26, the distal end portion 14d of the shaft 14 can extend into the proximal lumen 50 and can be secured in place, such as with an interference fit and/or a suitable adhesive.

The second connector portion 28 can include a distal end portion 54 and a proximal end portion 56. Each portion 54, 56 can have a generally cylindrical shape. In some embodiments, each portion 54, 56 can have a non-cylindrical shape (e.g., the cross-sectional shape of the portion can be square, oval, hexagonal, etc.). The outer surface of the distal end portion 54 can define a plurality of recesses 32 and optional bosses 34 extended therefrom, which form attachment features for forming a releasable connection with each of the retaining arms 84 of the prosthetic valve, as further described below. The second connector portion 28 can comprise a sidewall 58 defining a proximal lumen 62 along the proximal end portion 56 and a distal lumen 60 along the distal end portion 54, wherein the proximal lumen 62 can have a larger interior dimension (e.g., diameter) than the distal lumen 60.

In the exemplary embodiment depicted in FIGS. 5-6, the outer dimension of the distal end portion 44 of the first connector portion 26 is smaller than the interior dimension of the proximal lumen 62 of the second connector portion 28 such that there is a radial gap between the outer surface of the distal end portion 44 and the inner surface of the proximal lumen 62. Accordingly, the distal end portion 44 of the first connector portion 26 can be inserted into the proximal lumen 62 (which can also be referred to as an "axial bore") of the second connector portion 28. The respective lumens 50, 52, 62, and 60 of the first and second connector portions 26, 28 can collectively define a central passage for the inner shaft 18 to extend through.

In the exemplary embodiment depicted in FIG. 6, two pins 30', 30" extend radially outward from the distal end portion 44 of the first connector portion 26 respectively into two slots 40', 40" formed in the proximal end portion 56 of the second connector portion 28.

In some embodiments, the pins 30', 30" can be embedded in and extend radially outward from respective recesses 64', 64" located at the distal end portion 44 of the first connector portion 26. The recesses 64', 64", which can be formed in the sidewall 48 at diametrically opposed locations. The radial inner end portions of the pins 30, 30" can be secured in the recesses 64', 64", such as with an adhesive and/or a frictional fit. Alternatively, the sidewall 48 can be without recesses 64', 64" and the pins 30', 30" can be secured to the outer surface of the sidewall 48. Optionally, the pins 30', 30" can be formed as integral parts of the first connector portion 26 (i.e., they form a unitary piece) such that they protrude outwardly from the outer surface of the wall 48 without any recesses 64', 64". In the depicted embodiment, both slots 40', 40" extend through the sidewall 58 of the second connector portion 28, and they are arranged on opposite sides of the sidewall 58 with respect to the longitudinal axis 24. Each of the slots 40', 40" can have an arc length of less than 180 degrees.

Although the exemplary embodiment described herein have two pins 30 in two slots 40, it should be understood that any number of pins 30 and slots 40 (e.g., 1, 2, 3, 4, or more, etc.) can be used. Further, the slots 40 are not necessarily equally spaced circumferentially.

In the embodiments shown in FIGS. 4-6, the pins 30', 30" have a generally cylinder shape with a cross-sectional diameter D1. In some embodiments, the pins 30', 30" can have one or more other cross-sectional shapes (e.g., square, oval, hexagonal, etc.) with a maximum cross-sectional dimension D1. Each of the slots 40', 40", which defines an opening in the sidewall 58 of the second connector portion 28, has a circumferential dimension (or length) L measured circumferentially and an axial dimension (or width) W measured longitudinally over the outer surface of the second connector portion 28.

In some embodiments, the slot 40 can have an oversized circumferential dimension L (i.e., L>D1) or arc length (measured in degrees) that allows limited rotation (e.g., clockwise or counter-clockwise) of the second connector portion 28 relative to the first connector portion 26 about the longitudinal axis 24 of the shaft 14 (see e.g., FIGS. 2 and 9). The degree of rotational movement of the second connector portion 28 relative to the first connector portion 26 can be limited by the length (L) of the slot 40.

In addition, the slot 40 can have an oversized width W (i.e., W>D1) in a direction along the longitudinal axis 24 that allows limited axial movement (e.g., distally or proximally) of the second connector portion 28 relative to the first connector portion 26. The degree of axial movement of the second connector portion 28 relative to the first connector portion 26 can be limited by the width (W) of the slot 40.

The second connector portion 28 can also be configured to tilt relative to the first connector portion 26 about a tilt axis 82 (FIG. 4) defined by the pins 30, 30" by virtue of the arrangement of the distal end portion 44 of the first connector portion 26 with respect to the axial bore 62. For example, as noted above, the axial bore 62 of the second connector portion 28 can be oversized (e.g., in cross-sectional dimension) relative to the distal end portion 44 of the first connector portion 26 (e.g., D3>D2 as illustrated in FIG. 6) such that there is an annular or radial gap between the adjacent surfaces of the first and second connector portions. This allows the second connector portion 28 to tilt about the tilt axis 82 (in the directions indicated by double-headed arrow T in FIG. 2) wherein the tilt axis 82 extends through the pins 30', 30" perpendicular to the longitudinal axis 24. In this manner, the pins 30', 30" function as a fulcrum, allowing the second connector portion 28 to tilt relative to the first connector portion 26 about the tilt axis 82.

In addition, since the width W of the slots 40', 40" is greater than the dimension D1 of the pins 30', 30", the tilting motion of the second connector portion 28 relative to the first connector portion 26 is not necessarily limited to tilting motion about tilt axis 82 extending through the pins 30', 30". Explaining further, due to the width W being oversized relative to the dimension D1 and the diameter D3 being oversized relative to the diameter D2, the second connector portion 28 can "float" relative to the first connector portion 26 in three-dimensional space with movement of the second connector portion 28 being constrained by contact between the pins 30, 30" with the sides of the slots 40', 40". As such, the second connector portion 28 can shift and/or tilt relative to the first connector portion such that the central axis 88 of the second connector portion 28 (FIG. 8) deviates from the longitudinal axis 24 (i.e., movement of the second connector portion 28 causes the central axis 88 to become non-collinear with the longitudinal axis 24). Accordingly, in some embodiments, the second connector portion 28 can tilt and/or shift in any direction relative to the first connector portion 26, with movement of the second connector portion limited by the spacing or gap between the axial bore 62 and the distal end portion 44 of the first connector portion 26 and the spacing or gap between the pins 30, 30" and the sides of the slots 40', 40".

In some embodiments, as noted above, the second connector portion 28 can include one or more attachment features configured to form a releasable attachment with corresponding retaining arms of an implantable medical device, such as a prosthetic heart valve 80, retained in the device retaining portion 78 (see, e.g., FIGS. 1 and 3).

One exemplary, non-limiting embodiment of attachment features are shown in FIGS. 1-6. As depicted, the second connector portion 28 can have a plurality of circumferentially spaced recesses 32 formed in the outer surface of the distal end portion 54 and sized to receive respective retaining arms 84 of the prosthetic heart valve 80. Optional radially-extending bosses or pins 34 can be disposed within the plurality of recesses 32. Each boss 34 can be so complimentarily shaped and sized to engage with a corresponding aperture 86 in a retaining arm 84 of the prosthetic heart valve 80. Thus, by extending through the corresponding apertures 86, the bosses can serve as anchors to help secure the retaining arms 84 within the recesses. The distal end of the second connector portion can be formed with a flange 36 that has a slightly larger outer diameter than the section in which the recesses 32 are formed. The flange 36 can have one or more notches 38 along its circumferential edge. The notches 38 can be in communication with the recesses 32 such that the retaining arms 84 can extend through the notches.

When the prosthetic heart valve 80 is in a radially compressed state and attached to the delivery apparatus for delivery into a patient's body, the prosthetic heart valve 80 is positioned distal to the flange 36 within the retaining portion 78. The retaining arms 84 extend through the notches 32 in the flange 36 so as to position the end portions of the retaining arms 84 within respective recesses 32. The sheath 16 is extended over the prosthetic heart valve 80 to retain the retaining arms 84 within recesses 32 and to retain the prosthetic heart valve 80 in the radially compressed state.

Although FIG. 4 shows three recesses 32 (and three corresponding bosses 34 and notches 38) that are equally spaced circumferentially around the outer surface of the second connector portion 28, it should be understood that any number of recesses 32 (and corresponding bosses 34 and notches 38) can be included so long as they collectively engage with the respective retaining arms 84 of the prosthetic heart valve 80. Further, it should be understood that the attachment features can take any other forms so long as to enable releasable attachment with the implantable medical device. For example, in some embodiments, the attachment features can include a suture retention member and a slidable release member, as disclosed in US 2014/0343670, which is incorporated by reference herein.

After attaching the prosthetic heart valve 80 to the delivery apparatus 12 as described above, the delivery apparatus can be inserted in the vasculature of a patient (e.g., a femoral artery and the aorta when delivering a prosthetic aortic valve in a retrograde delivery approach). Because the implantable medical device can be releasably attached to the second connector portion 28, the connector assembly 20 in the illustrated embodiment supports limited, multiple degrees of movement of the implantable medical device retained within the outer sheath 16 at the device retaining portion 78. As a result, the connector assembly 20 can function as a flexible self-tracking joint, such that when pushing the delivery apparatus 12 through a patient's vasculature, the distal portion of the delivery apparatus 12 (and the implantable medical device retained therein) can more easily track or follow the contour of the vasculature by passive deflections, for example, in one embodiment, in at least three independent degrees of freedom (by limited tilting, rotation, and/or translation) against resistance from the vascular wall. Such self-tracking capability is advantageous because it allows the physician to more easily navigate the delivery apparatus 12 through a challenging vascular path, and in some embodiments reducing or even eliminating the need to operate control mechanisms for steering the delivery apparatus 12 (e.g., actively bending the distal portion through pull wires to achieve a desired curvature).

Figure 7A:
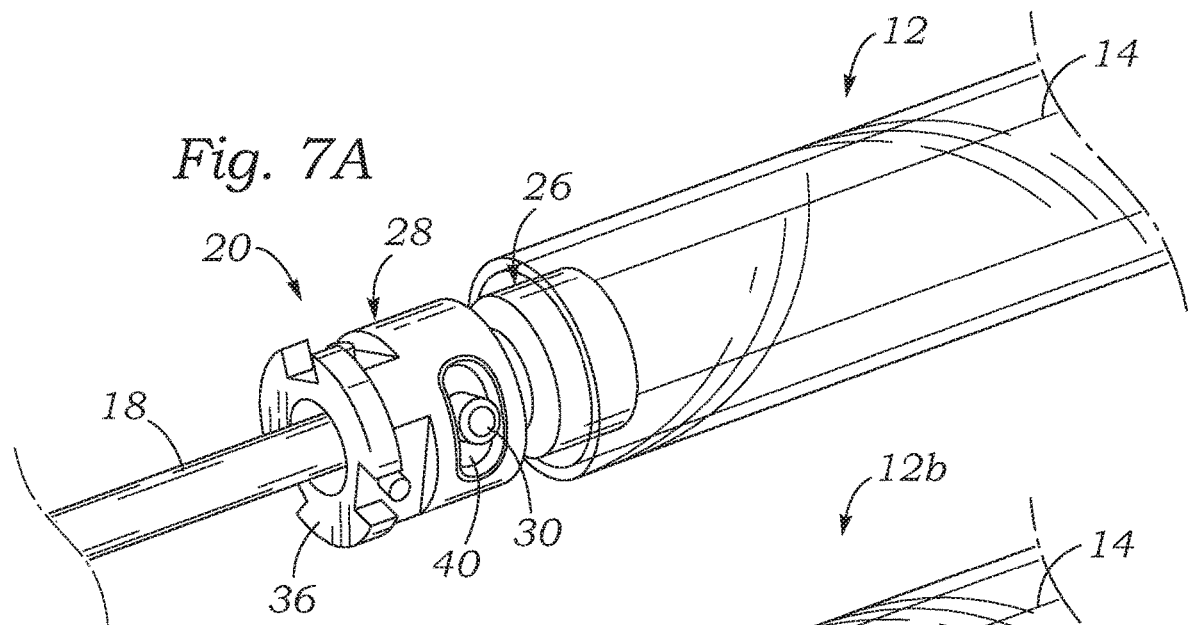
FIG. 7A shows an enlarged view of an exemplary connector assembly and its coupling with a shaft of the delivery apparatus.

FIG. 7A shows an enlarged view of the connector assembly 20 and its coupling with the shaft 14 of the delivery apparatus 12 depicted in FIG. 2.

Figure 7B:
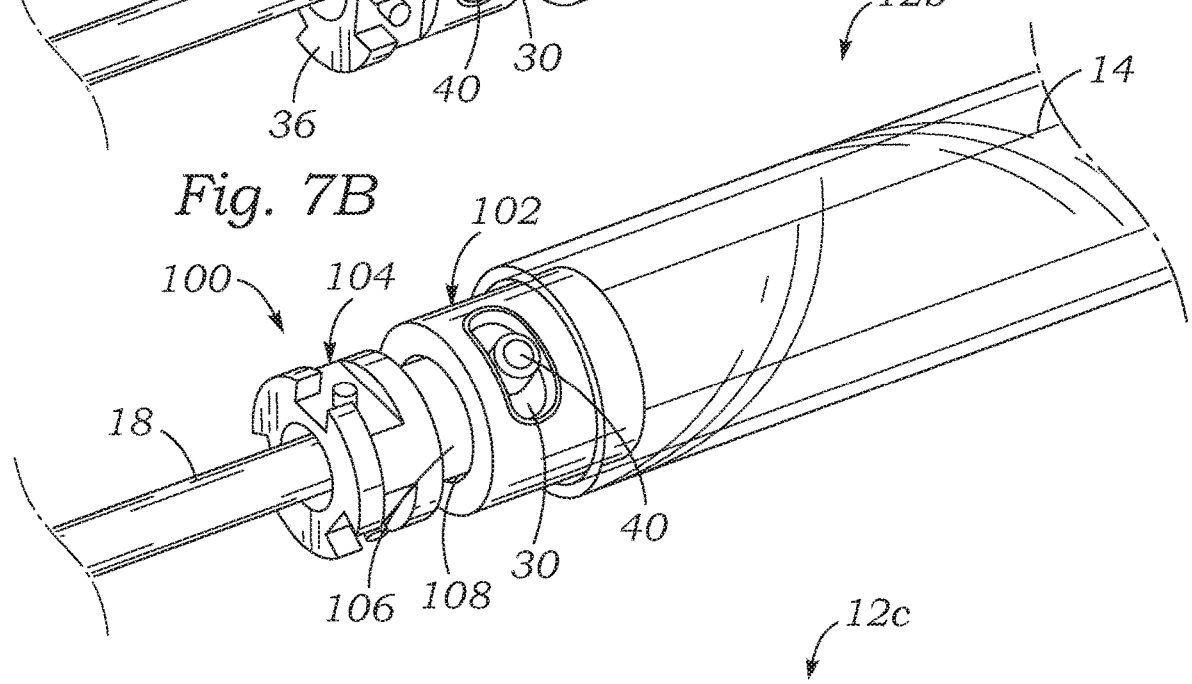
FIG. 7B shows an exemplary embodiment of the connector assembly and its coupling with a shaft of the delivery apparatus.

FIG. 7B shows an exemplary connector assembly 100 incorporated in the delivery apparatus 12*b*, which can be used in place of and/or similarly to connector assembly 20. The connector assembly 100 comprises the first and second connector portions 102, 104, respectively (which can be the similar to portions 26, 28 and/or can include similar features, components, etc.). The first connector portion 102 is fixedly coupled to the shaft 14, and the inner shaft 18 extends through the shaft 14 and the connector assembly 100.

In the illustrated embodiment, the second connector portion 104 has a proximal end portion 106 which has an outer diameter that is smaller than the interior diameter of a distal lumen 108 of the first connector portion 102. Accordingly, the proximal end portion 106 of the second connector portion 104 can extend into the distal lumen 108 of the first connector portion 102.

In addition, the first and second connector portions 102, 104 can be rotatably coupled to each other by one or more pins 30 extending radially outwardly from the second connector portion 104 and retained within respective slots 40 on the first connector portion 102. Similarly, a distal lumen 108 of the first connector portion 102 can be oversized relative to a proximal end portion 106 of the second connector portion 28*b*, and the slots 40 can be oversized in length and width relative to the cross-sectional dimensions of the pins 30 so that the second connector portion 104 can have a limited degree of freedom to rotate around the longitudinal axis 24, and/or translate along the longitudinal axis 24, and/or tilt in any direction relative to the first connector portion 102.

Figure 7C:
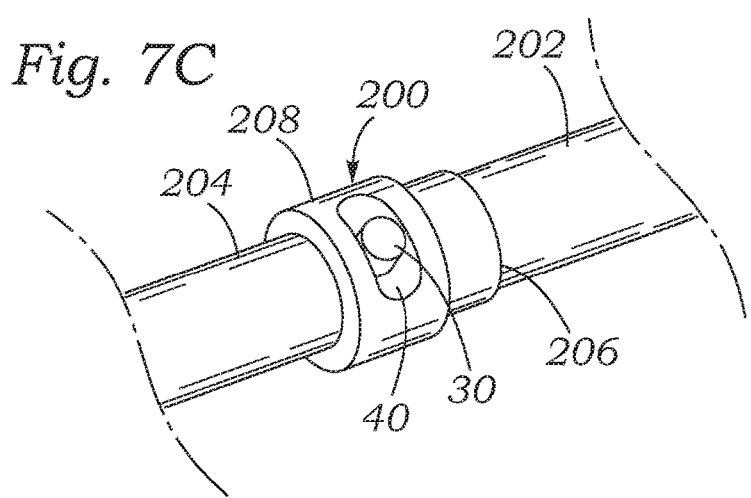
FIG. 7C shows an exemplary embodiment of the connector assembly and its coupling with a shaft of the delivery apparatus.

FIG. 7C shows an exemplary connector assembly 200 incorporated in a delivery apparatus 12*c*, which can be used in place of and/or similarly to connector assembly 20 or 100. The connector assembly 200 comprises a first connector portion 206 and a second connector portion 208 (which can be the similar to portions 26, 28 or portions 102, 106, and/or can include similar features, components, etc.). The first connector portion can be fixedly coupled to a first shaft segment 202, and the second connector portion can be fixedly coupled to a second shaft segment 204. Similar to the connector assembly 20, the first and second connector portions 206, 208 can be rotatably coupled to each other by one or more pins 30 extending from the first connector portion 206 and retained within respective slots 40 on the second connector portion 208.

The connector assembly 200 can have the same configuration as the connector assembly 20 previously described and include similar features, except that the second connector portion 208 is not formed with any retaining features for retaining an implantable medical device. Instead, the connector assembly 200 is used as a linkage between adjacent ends of two shaft segments of a catheter assembly. Similar to the connector assembly 20, a proximal lumen of the second connector portion 208 can be oversized relative to a distal end portion of the first connector portion 206, and the slots 40 can be oversized in length and width relative to the cross-sectional dimensions of the pins 30 so that the second connector portion 208 can have limited rotational, axial, and/or tilting movement relative to the first connector portion 206. Because the second shaft segment 204 is fixedly coupled to the second connector portion 208, any rotational, axial, and/or tilting movement of the second connector portion 208 can also cause corresponding rotational, axial, and/or tilting movement of the second shaft segment 204 relative to the first shaft segment. In this manner, the connector assembly 200 increases the flexibility of the shaft assembly along its length.

Although only two shaft segments are generally shown in the various embodiment of the figures, it should be understood that a shaft assembly can comprise any number of shaft segments coupled to end-to-end with respective connector assemblies (e.g., 1, 2, 3, 4, 5, 6, or more connector assemblies 20, 100, 200 connected to multiple shaft segments) to enhance the flexibility of the shaft assembly along its length. A variety of different types of connector assemblies (e.g., assemblies 20, 100, 200) can be used in different locations along a shaft assembly as well. Each shaft segment of the multi-segment hinged shaft assembly can have a limited degree of rotational, axial, and/or tilting movement relative to an attached connector assembly and an adjacent shaft segment. In one implementation, connector assemblies can be used to interconnect relatively short, non-flexible shaft segments, such as metal shaft segments, to form a shaft assembly with a high degree of flexibility.

In FIGS. 7A-7C, the pins extend radially outwardly and are retained in respective outer slots. For example, in FIG. 7A (and similarly in FIG. 7C), because the distal end portion 44 of the first connector portion 26 is inserted into the proximal lumen 62 of the second connector portion 28, the slots 40 retaining the pins 30 are positioned exterior to the distal end portion 44 from which the pins 30 extend radially outward. In FIG. 7B, because the proximal end portion 106 of the second connector portion 104 is inserted into the distal lumen 108 of the first connector portion 102, the slots 40 retaining the pins 30 are also positioned exterior to the proximal end portion 106 from which the pins 30 extend radially outward.

Although not shown, it should be understood that the pin-in-slot configuration can be structured differently such that the pins can extend inwardly and are retained in respective inner slots. For example, the connector assembly can have an inner portion inserted into the central lumen of an outer portion, and the pins can extend radially inward from the outer portion and be retained within corresponding inner slots located on the inner portion. The inner portion can be part of the first connector portion and the outer portion can be part of the second connector portion. Optionally, the inner portion can be part of the second connector portion and the outer portion can be part of the first connector portion. Similarly, the inner slots can be oversized relative to the inwardly extending pins so that the second connector portion can have limited rotational, axial, and/or tilting movement relative to the first connector portion.

General Considerations

The disclosed embodiments can be adapted to deliver and implant prosthetic devices in any of the native annuluses/valves of the heart (e.g., the pulmonary, mitral, and tricuspid annuluses/valves), and can be used with any of various delivery approaches (e.g., retrograde, antegrade, transseptal, transventricular, transatrial, transvascular, etc.) or other organs.

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved. The technologies from any example can be combined with the technologies described in any one or more of the other examples. In view of the many possible embodiments to which the principles of the disclosed technology may be applied, it should be recognized that the illustrated embodiments are only preferred examples and should not be taken as limiting the scope of the disclosed technology.

Although the operations of some of the disclosed embodiments are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

As used in this application and in the claims, the singular forms "a," "an," and "the" include the plural forms unless the context clearly dictates otherwise. Additionally, the term "includes" means "comprises." Further, the terms "coupled" and "connected" generally mean electrically, electromagnetically, and/or physically (e.g., mechanically or chemically) coupled or linked and does not exclude the presence of intermediate elements between the coupled or associated items absent specific contrary language.

Directions and other relative references (e.g., inner, outer, upward, downward, interior, exterior, etc.) may be used to facilitate discussion of the drawings and principles herein, but are not intended to be limiting. For example, certain terms may be used such as "inside," "outside,", "top," "down," and the like. Such terms are used, where applicable, to provide some clarity of description when dealing with relative relationships, particularly with respect to the illustrated embodiments. Such terms are not, however, intended to imply absolute relationships, positions, and/or orientations. For example, with respect to an object, an "upper" part can become a "lower" part simply by turning the object over. Nevertheless, it is still the same part and the object remains the same. As used herein, "and/or" means "and" or "or", as well as "and" and "or".

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims and encompasses all that falls within the scope of these claims.

What is claimed is:

1. A catheter assembly, comprising:
   a shaft; and
   a connector assembly comprising a first connector portion and a second connector portion, wherein the first connector portion is fixedly coupled to a distal end of the shaft, and is rotatably coupled to the second connector portion by at least one radially extending pin retained within at least one slot on the second connector portion, wherein the at least one slot has an oversized circumferential dimension that allows limited rotation of the second connector portion relative to the first connector portion about a longitudinal axis of the shaft, wherein the at least one slot has an oversized width in a direction along the longitudinal axis that allows limited axial movement of the first connector portion relative to the second connector portion.

2. The catheter assembly of claim 1, wherein the at least one slot is sized to allow limited tilting of the second connector portion with respect to the longitudinal axis of the shaft.

3. The catheter assembly of claim 1, wherein the at least one slot comprises first and second slots and the at least one pin comprises first and second pins disposed in the first and second slots, respectively.

4. The catheter assembly of claim 3, wherein each slot has an arc length around the longitudinal axis of less than 180 degrees.

5. The catheter assembly of claim 1, wherein the first connector portion comprises a distal end portion that extends into an axial bore of the second connector portion, and the at least one pin extends radially outwardly from the distal end portion into the at least one slot in the second connector portion.

6. The catheter assembly of claim 1, wherein the second connector portion comprises one or more attachment features configured to form a releasable attachment with corresponding retaining arms of an implantable medical device.

7. The catheter assembly of claim 6, wherein the one or more attachment features comprise one or more recesses configured to receive the one or more retaining arms of the implantable medical device.

8. The catheter assembly of claim 6, further comprising an outer sheath configured to extend over the connector assembly and the implantable medical device so as to retain the implantable medical device in a radially compressed state within the sheath when the retaining arms are in engagement with the attachment features of the second connector portion.

9. The catheter assembly of claim 1, further comprising another shaft having a proximal end connected to the second connector portion.

10. A delivery apparatus for delivering an implantable device via a patient's vasculature, comprising:
    an outer sheath;
    a shaft extending through the outer sheath; and
    a connector assembly comprising a first connector portion and a second connector portion, the first connector portion being fixedly coupled to a distal end of the shaft, the second connector portion being coupled to the first connector portion such that the second connector portion can rotate relative to the first connector portion about a longitudinal axis of the shaft and can tilt with respect to the longitudinal axis of the shaft;
    wherein the second connector portion comprises one or more attachment features configured to form a releasable attachment with corresponding retaining arms of a radially expandable implantable medical device;
    wherein the outer sheath is configured to extend over the connector assembly and the implantable medical device so as to retain the implantable medical device in a radially compressed state within the sheath when the retaining arms of the implantable medical device are placed in engagement with the attachment features of the second connector portion;
    wherein the second connector portion is coupled to the first connector portion such that the second connector portion can move axially relative to the first connector portion a limited amount in a direction parallel to the longitudinal axis.

11. The delivery apparatus of claim 10, wherein the second connector portion is coupled to the first connector portion by at least one radially extending pin retained within at least one slot on the second connector portion.

12. The delivery apparatus of claim 11, wherein the at least one slot has an oversized circumferential dimension that allows limited rotation of the second connector portion relative to the first connector portion about the longitudinal axis of the shaft.

13. The delivery apparatus of claim 10, wherein the second connector portion is coupled to the first connector portion by at least one radially extending pin retained within at least one slot of the first connector portion.

14. The delivery apparatus of claim 10, wherein the at least one slot is sized to allow limited tilting of the second connector portion with respect to the longitudinal axis of the shaft.

15. The delivery apparatus of claim 10, wherein the attachment features of the second connector portion comprise one or more recesses configured for receiving one or more retaining arms of the implantable device.

16. A delivery apparatus for delivering an implantable device via a patient's vasculature, comprising:
an outer sheath;
a shaft extending through the outer sheath; and
a connector assembly comprising a first connector portion and a second connector portion, the first connector portion being fixedly coupled to a distal end of the shaft, the second connector portion being coupled to the first connector portion such that the second connector portion can rotate relative to the first connector portion about a longitudinal axis of the shaft and can tilt with respect to the longitudinal axis of the shaft;
wherein the second connector portion comprises one or more attachment features configured to form a releasable attachment with corresponding retaining arms of a radially expandable implantable medical device;
wherein the outer sheath is configured to extend over the connector assembly and the implantable medical device so as to retain the implantable medical device in a radially compressed state within the sheath when the retaining arms of the implantable medical device are placed in engagement with the attachment features of the second connector portion;
wherein the at least one slot has an oversized width in a direction along the longitudinal axis that allows limited axial movement of the first connector portion relative to the second connector portion.

17. A delivery apparatus for delivering an implantable device via a patient's vasculature, comprising:
an outer sheath;
a shaft extending through the outer sheath; and
a connector assembly comprising a first connector portion and a second connector portion, the first connector portion being fixedly coupled to a distal end of the shaft, the second connector portion being coupled to the first connector portion such that the second connector portion can rotate relative to the first connector portion about a longitudinal axis of the shaft and can tilt with respect to the longitudinal axis of the shaft;
wherein the second connector portion comprises one or more attachment features configured to form a releasable attachment with corresponding retaining arms of a radially expandable implantable medical device;
wherein the outer sheath is configured to extend over the connector assembly and the implantable medical device so as to retain the implantable medical device in a radially compressed state within the sheath when the retaining arms of the implantable medical device are placed in engagement with the attachment features of the second connector portion;
wherein the at least one slot comprises first and second slots and the at least one pin comprises first and second pins disposed in the first and second slots, respectively, and the first slot being opposite the second slot with respect to the longitudinal axis.

18. An assembly, comprising:
an outer sheath;
a first shaft extending through the outer sheath;
a second shaft extending through the first shaft;
a nose cone mounted on a distal end portion of the second shaft;
a connector assembly comprising a proximal connector portion and a distal connector portion, the proximal connector portion being fixedly coupled to a distal end of first shaft, the distal connector portion being rotatably coupled to the proximal connector portion by at least a pin retained within a slot in the distal connector portion, wherein the slot has an oversized circumferential dimension that allows limited rotation of the distal connector portion relative to the proximal connector portion about a longitudinal axis of the first shaft, limited tilting of the distal connector portion with respect to the longitudinal axis, and limited axial movement of the distal connector portion relative to the proximal connector portion in a direction parallel to the longitudinal axis, wherein the distal connector portion comprises one or more attachment features; and
a radially expandable and compressible prosthetic heart valve retained in a radially compressed state within the sheath and having one or more retaining arms that engage respective attachment features of the distal connector portion.

* * * * *